(12) United States Patent
Heger et al.

(10) Patent No.: US 8,168,220 B2
(45) Date of Patent: May 1, 2012

(54) DOSAGE FORMS OF ACTIVE INGREDIENTS CONTAINING HYDROXYSTILBENE FOR TREATING MENOPAUSAL COMPLAINTS

(76) Inventors: Peter Heger, Ubstadt-Weiher (DE); Reinhard Rettenberger, Goppingen (DE); Carl-Friedrich Spaich, Heiningen (DE)

(*) Notice: Subject to any disclaimer, the term of this patent is extended or adjusted under 35 U.S.C. 154(b) by 879 days.

(21) Appl. No.: 11/883,667

(22) PCT Filed: Feb. 3, 2006

(86) PCT No.: PCT/EP2006/000957
§ 371 (c)(1),
(2), (4) Date: Apr. 25, 2008

(87) PCT Pub. No.: WO2006/082073
PCT Pub. Date: Aug. 10, 2006

(65) Prior Publication Data
US 2008/0248069 A1    Oct. 9, 2008

(30) Foreign Application Priority Data

Feb. 4, 2005 (DE) .......... 10 2005 005 268
Feb. 4, 2005 (DE) .......... 10 2005 005 271

(51) Int. Cl.
*A61K 9/20* (2006.01)
(52) U.S. Cl. ........ 424/464; 424/773; 435/375; 514/729; 514/25
(58) Field of Classification Search .................. None
See application file for complete search history.

(56) References Cited

U.S. PATENT DOCUMENTS

| | | | |
|---|---|---|---|
| 2002/0173472 A1 | 11/2002 | Pezzuto et al. | |
| 2008/0026086 A1* | 1/2008 | Holyoak et al. | 424/770 |
| 2009/0042817 A1 | 2/2009 | Heger et al. | |
| 2009/0048184 A1 | 2/2009 | Heger et al. | |
| 2009/0137496 A1 | 5/2009 | Heger et al. | |

FOREIGN PATENT DOCUMENTS

| EP | 0 704 208 A | 4/1996 |
|---|---|---|
| FR | 2 835 185 A | 8/2003 |
| FR | 2835185 | 8/2003 |
| WO | WO 00/12534 A | 3/2000 |
| WO | WO 01/08671 A | 2/2001 |
| WO | WO 01/21165 A | 3/2001 |

OTHER PUBLICATIONS

Rote Liste Service GMGH (Ed.): "Rote Liste, 2002, Editio Cantor Verlag, Aulendorf, Eintrag 76001 "Phytoestrol N"".*
Wober, et al., Journal of Steroid Biochemistry and Molecular Biology 107 (2007) 191-201.*
Kaszkin-Bettag et al., Alternative Therapies. Jan./Feb. 2009. vol. 15, No. 1.*
Abstract for Aerztezeitung May 16, 2000, "Phytoestrogen hilft bei Beschwerden im Klimakterium". (English Translation).
Beral et al., Lancet 2002; 360: 942-944.
Chlebowsky et al., JAMA 2003; 289: 3243-3253.
Colditz et al., New England Journal of Medicine 1995; 332: 1589-1593.
Collaborative Group, Lancet 1997; 359: 1047-1059.
Frasor et al., Endocrinology 2003: 144: 3159-3166.
Ginsburg, Obstetrics and Gynecology Clinics of North America 1994, 21 (2), 38-390.
Hewitt et al., Breast Cancer Research 2000; 2: 345-352.
Lindberg et al., Mol Endocrinol 2003; 17: 203-208.
Magnusson et al. Int J. Cancer 1999; 81: 339-344.
Million Women Study Collaborators, Lancet 2003; 362: 419-427.
Mueller et al., Toxicol. Sci. 2004; 80: 14-25.
Park et al., Arch. Pharm. Res. 2002, 25 (4), 528-533.
Ross et al., J. Natl. Cancer Inst. 2000; 92: 328-332.
Schairer et al., JAMA 2000; 283: 485-491.
Unfer et al., Fertil Steril 2004; 82: 145-148.
Writing Group for WHI Investigators, JAMA 2002; 288: 321-333.
Rote Liste Service GMGH (Ed.): Rote Liste:, 2002, Editio Cantor Verlag, Aulendorf, XP002379296, Eintrag 76001 "Phytoestrol N".
Anonym: "Phytoesrogen hilft bei Beschwerden im Klimakterium" Arzte Zeitung, [Online] May 16, 2000, XP002378130, Retrieved from the Internet: URL:http://www.aerztezeitung.de/docs/2000/05/16/089a1403.asp?cat=> [retrieved on Apr. 24, 2006, the whole document.

* cited by examiner

*Primary Examiner* — Robert A Wax
*Assistant Examiner* — Hasan Ahmed
(74) *Attorney, Agent, or Firm* — Edwards Wildman Palmer LLP; Peter C. Lauro, Esq.; Weiying Yang, Esq.

(57) ABSTRACT

The invention relates to novel dosage forms containing hydroxystilbene, to a method for producing said dosage forms and to their use for treating female menopausal complaints, juvenile oligomenorrhoea and dysmenorrhoea, primary and secondary amenorrhoea or endometritis.

28 Claims, 4 Drawing Sheets

DOSAGE FORMS OF ACTIVE INGREDIENTS CONTAINING HYDROXYSTILBENE FOR TREATING MENOPAUSAL COMPLAINTS

This application is the U.S. national phase application, pursuant to 35 U.S.C. §371, of PCT international application Ser. No. PCT/EP2006/000957, filed Feb. 3, 2006, designating the United States and published in German on Aug. 10, 2006 as publication WO 2006/082073 A1, which claims priority to German application Ser. Nos. DE 10 2005 005 268.1, filed Feb. 4, 2005 and DE 10 2005 005 271.1, filed Feb. 4, 2005. The entire contents of the aforementioned patent applications are incorporated herein by this reference.

The invention relates to novel hydroxystilbene-containing dosage forms, processes for producing these dosage forms and the use thereof for the treatment of menopausal symptoms in women, juvenile oligomenorrhea and dysmenorrhea, primary and secondary amenorrhea or endometritis.

BACKGROUND OF THE INVENTION

The menopause is an impairment of ovarian function accompanied by high levels of follicle-stimulating hormone (FSH) and lower levels of estradiol (E2). The time up to the last menstruation is also referred to as "perimenopause". During this period, most women notice cycle irregularities which last for 1 to 5 years. In most western countries, about 80% of peri- and postmenopausal women suffer from hot flushes, in about 30% of them the hot flushes are so severe and frequent that the quality of life is noticeably impaired thereby. The exact physiological cause of hot flushes is unknown (Ginsburg, Obstetrics and Gynecology Clinics of North America 1994; 21 (2): 381-390). Hot flushes follow a release of gonadotropin-releasing hormone (GnRH) from the hypothalamus and are not linked to changes in the level of estradiol and estrone. They are accompanied by the release of luteinizing hormone (LH), corticotrophin, growth hormone and β-lipotrophin from the pituitary and of dehydroepiandrosterone and androstenedion from the adrenal. FSH levels may vary between normal and high (>20 IU/l).

Hormone replacement therapy (HRT) replaces the two female sex steroids estrogen and progesterone. HRT was employed for many years for the treatment of menopausal symptoms and for preventing cardiovascular disorders and osteoporosis in the peri- and postmenopause. It was regarded as effective and safe. However, this is no longer true since large randomized controlled studies were carried out and showed the contrary (Beral et al., Lancet 2002; 360: 942-944, Collaborative Group, Lancet 1997; 359: 1047-1059). HRT has no positive effect on the incidence and progression of coronary heart disease. There is in fact evidence that it increases the risk of cardiovascular disorders in peri- and post menopausal women. In a randomized, placebo-controlled double-blind study of primary prevention with estrogen plus progestin, carried out by the Women's Health Initiative (WHI), 100% more thromboses, 41% more strokes and 29% more myocardial infarctions compared with placebo found after HRT (Writing Group for WHI Investigators JAMA 2002; 288: 321-333, Chlebowsky et al. JAMA 2003; 289: 3243-3253). In addition, it has been found in randomized controlled studies that HRT is linked to an increased risk of the occurrence of breast cancer (Million Women Study Collaborators Lancet 2003; 362: 419-427, Schairer et al. JAMA 2000; 283: 485-491, Ross et al. J Natl Cancer Inst 2000; 92: 328-332, Colditz et al. N Engl J Med 1995; 332: 1589-1593, Magnusson et al. Int J Cancer 1999; 81: 339-344).

The estrogen receptor (ER) mediates the activity of estrogens in regulating a number of important physiological processes, including the development and function of the female reproductive system. Whereas stimulation of processes in these tissues has important health advantages, the cancer risk may be increased by stimulation of other tissues such as the breast and the uterus, especially in the peri- and postmenopause. The ER family comprises two subtypes, namely ERα and ERβ. Studies with ER-selective knockout mice have shown that the typical unwanted estrogen effects such as endometrial hyperplasia and breast cancer are mediated by ERα, or as ERβ acts as a negative regulator of ERα and is important for protecting against hyperproliferation and carcinogenesis in tissues in which both receptors are coexpressed (Hewitt et al. Breast Cancer res 2003; 2: 345-352, Frasor et al. Endocrinology 2003; 144: 3159-3166, Lindberg et al. Mol Endocrinol 2003; 17: 203-208).

Based on the results of clinical and experimental studies, increasing numbers of women refuse to use HRT for their menopausal symptoms. In addition, HRT is not indicated for treating women who already have an endocrine-dependent tumor, or show a high cancer risk, especially breast cancer and endometrial cancer. For these reasons, novel active ingredients for treating menopausal symptoms which are free of the potential risks associated with HRT, especially also on long-term use, are very desirable.

There are a number of so-called phytoestrogens which have claims to be effective in relation to reducing hot flushes and sweating episodes. For most of these herbal products, the results of clinical studies, where in fact available, are contradictory or show no efficacy by comparison with placebo. In addition, some constituents of these products may have an estrogenic activity despite their relatively weak binding affinity for ERα (e.g. genistein, coumestrol, equol and zearalenone; Müller et al. Toxicol. Sci. 2004; 80: 14-25) and thus represent the risks similar to HRT. It has in fact been observed that long-term treatment with soya phytoestrogens led to endometrial hyperplasia (Unfer et al., Fertil Steril 2004; 82: 145-148). These observations cast doubt on the long-term safety of phytoestrogens, especially in relation to the endometrium.

There is thus a great need for novel active ingredients or active ingredient combinations for treating menopausal symptoms which do not bind to ERα, i.e. are not procarcinogenic, and do not promote the development of cardiovascular disorders.

Since 1993, a dry extract of roots of *Rheum rhaponticum* has been on the market in Germany under the name Extrakt *Rheum rhaponticum* (ERr 731®) (proprietary name Phytoestrol® N) for follicle hormone replacement therapy, for example for treating women with menopausal symptoms, juvenile oligomenorrhea and dysmenorrhea, primary and secondary amenorrhea, and endometritis. The constituents of the specific ERr 731® extract are rhaponticin, deoxyrhaponticin, rhapontigenin and deoxyrhapontigenin (table 1).

TABLE 1

Composition of the extract ERr 731 ®

| Hydroxystilbene | Chemical name | CAS No. |
|---|---|---|
| Rhaponticin | 3,3',5-Trihydroxy-4'-methoxystilbene 3-O-β-D-glucopyranoside | 155-58-8 |
| Deoxyrhaponticin | 3',5-Dihydroxy-4'-methoxystilbene 3-O-β-D-glucopyranoside | 30197-14-9 |

TABLE 1-continued

Composition of the extract ERr 731 ®

| Hydroxystilbene | Chemical name | CAS No. |
|---|---|---|
| Rhapontigenin (trans-Rhapontigenin) | 3,3',5-Trihydroxy-4'-methoxystilbene | 500-65-2 |
| Deoxyrhapontigenin | 3',5-Dihydroxy-4'-methoxystilbene | 33626-08-3 |

All of the constituents of ERr 731® belong to the group of hydroxystilbenes. Several studies have shown that the number and position of the free hydroxy and methoxy groups strongly influences the biological activity of the hydroxystilbenes. The pharmacological effect of the hydroxystilbenes is moreover dependent on the presence of a glucose group.

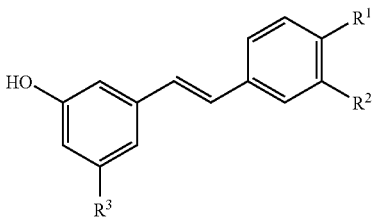

| | $R^1$ | $R^2$ | $R^3$ |
|---|---|---|---|
| Resveratrol | OH | H | OH |
| Rhaponticin | $OCH_3$ | OH | O-Glc |
| Deoxyrhaponticin | $OCH_3$ | H | O-GLc |
| Rhapontigenin | $OCH_3$ | OH | OH |
| Deoxyrhapontigenin | $OCH_3$ | H | OH |
| Astringin | OH | OH | O-Glc |
| Piceatannol (astringenin) | OH | OH | OH |

There has been only inadequate investigation of whether, and to which metabolites, the constituents of ERr 731® are degraded in the body for example after oral administration. Thus, it is merely known from investigations on the antithrombotic and antiallergic activity of rhaponticin-containing extracts from rhizoma rhei that rhaponticin is degraded by bacteria of the human intestinal tract to rhapontigenin (Park et al, Arch. Pharm. Res. 2002, 25 (4), 528-533). Metabolism of rhaponticin to piceatannol or of deoxyrhaponticin to resveratrol has not been observed to date.

The commercially available product ERr 731® (proprietary name Phytoestrol® N) shows certain disadvantages in relation to dosage form and production. In particular, the absolute active ingredient content in the commercial product is relatively low, so that the dosage form for a dose of, for example, 4 mg of active ingredient is relatively large (400 mg tablet), which is found on occasion to be disadvantageous for oral administration.

The size of the dosage form additionally has disadvantageous effects on the production costs, because a disproportionately large content of formulation ancillary substances is present relative to the amount of active ingredient, in turn unnecessarily increasing the production costs. A size reduction of the solid dosage form is not easily achieved, since when the size of the dosage form is reduced, the limit for the permissible variation in active ingredient content becomes increasingly difficult to comply with. This is true in particular of active ingredients of the present type, which are very prone to become inhomogeneous during production of the solid dosage form, especially of the active ingredient-containing tablet core.

Since active ingredient release in the intestine is desired in some cases for the solid dosage forms employed for the above indication, conventional formulations are provided with a gastro-resistant coating. Coatings of this type usually include a plasticizer, to prevent unwanted formation of cracks, which frequently leads to intolerances such as, for example, allergies, especially on prolonged intake of the medicament. On the other hand, if cracks occur there is the risk of causing stomach ache. Crack resistant but plasticizer-free, gastro-resistant solid formulations would therefore likewise be desirable.

Disadvantages of solid oral dosage forms currently on the market are on occasion also to be seen in the fact that the ingredients are unable to act immediately because the release takes place only with a certain time lag, and thus treatment of acute symptoms such as suddenly occurring migraines or hot flushes is not optimal. In addition, conventional solid dosage forms can be administered only systemically and not locally, this being disadvantageous in the case of locally restricted health impairments such as, for example, the occurrence of vaginal problems with no other menopausal symptoms in addition. Moreover, individual dosage of solid dosage forms, especially gastro-resistant tablets, is possible to only a limited extent because they are not divisible, which likewise may be disadvantageous. Alternative dosage forms, which can be employed as required, of the above active ingredients would therefore be desirable.

Against the provision of dosage forms which are not designed for oral administration, such as, for example, gels for local application, is also the fact that it has to date been assumed that the resveratrol and piceatannol precursors such as rhaponticin and deoxyrhaponticin are pharmacologically inactive per se and show an effect only through metabolism to resveratrol and piceatannol after oral administration.

FR 2 835 185 describes a complex rhubarb extract obtainable from rhizomes of Rheum rhaponticum, which is said to be characterized in that it comprises at least 50% hydroxystilbenes, with at least 50% of these hydroxystilbenes consisting of rhaponticin, deoxyrhaponticin, astrangin and piceatannol. A preferred extract comprises 15-50% by weight rhaponticin, 10-35% by weight deoxyrhaponticin, 5-10% by weight astrangin and 0.1-3% by weight piceatannol. This extract is, as illustrated in the examples, prepared by hydroalcoholic extraction of rhizomes of Rheum rhaponticum. The total content of rhaponticin and deoxyrhaponticin which can be obtained thereby is only 76% by weight. The content of astrangin comprises 11% by weight, the content of piceatannol comprises 3% by weight, and the content of anthracenosides comprises 0.5% by weight. In addition thereto, this extract appears to comprise about 10% by weight further undefined constituents. It is additionally asserted in FR 2 835 185 that the specific extract therein has, as a result of alleged synergistic effects of the various ingredients of the extract, biological properties which are considerably superior to the effect of the individual hydroxystilbenes, especially those effects which the ingredients described therein are said to have individually. The extract described therein is alleged to have antioxidant, antitumor, antiinflammatory and estrogenic properties. However, in fact, FR 2 835 185 does not provide a verifiable technical teaching for the asserted pharmacological usability, to say nothing of the asserted synergistic effect of the complex drug extract described therein. The experimental section describes merely individual formulation examples of capsules, tablets or creams. In particular, experimental data proving the alleged usability for the treatment of disorders connected with free radicals, such as, for example, accelerated aging, cancer, arteriosclerosis, wrinkles, inflammatory phenomena and the like, are completely lacking. The asserted suitability of a combination of the rhubarb extract described therein with a hop extract rich in prenyl flavonoids for the treatment of diseases standing with free radicals and/or for the treatment of hormonal imbalance such as amenorrhea, menopause, hot flushes etc., is not proved by any data either. It is moreover entirely unclear which of the components actually present in the extract described therein (rhaponticin, deoxyrhaponticin, astrangin, piceatannol, anthracenosides, and the unanalyzed constituents present in a content of 10%) contribute to the asserted pharmacological activity or, where appropriate, are in fact absolutely necessary for the asserted synergism. The actual disclosure of FR 2 835 185 should therefore be restricted to the preparation of a specific, complex rhubarb extract by hydroalcoholic extraction of rhizomes of *Rheum rhaponticum* and the preparation of specific hydroxystilbene derivatives, and the production of various pharmaceutical formulations. In addition, there are doubts whether the complex extract disclosed in FR 2 835 185 can in fact be processed satisfactorily to tablets complying with the quality standards of the pharmaceutical industry.

There is thus a need for improved dosage forms for the extract ERr 731 and other compositions with similar active ingredients for more efficient treatment of various menopausal disorders which no longer have one or more of the disadvantages described above.

SUMMARY OF THE INVENTION

This object has surprisingly been achieved by providing solid dosage forms, which can easily be produced, of ERr 731® and comparable active ingredients and active ingredient combinations, which may additionally have a higher active ingredient content. The above object has also been achieved by providing for the first time semisolid and liquid dosage forms of the active ingredients and combinations thereof described above.

This is because the following has surprisingly been found:
a) Smaller solid dosage forms with a higher relative active ingredient content, which have a surprisingly small percentage variation in the active ingredient content, can be produced.
b) Smaller solid dosage forms with a higher relative active ingredient content and gastro-resistant coating are in addition more crack resistant than conventional tablets and can be formulated without plasticizer in the coating, whereby fewer side effects occur, such as gastric problems and allergies, because of the absence of plasticizers.
c) Because of the surprisingly found activity of resveratrol and piceatannol precursors such as rhaponticin and deoxyrhaponticin per se, it is possible to provide liquid or semisolid formulations which include these active ingredients and can be administered locally, can be individually dosed better and more accurately, make the active ingredient bioavailable more quickly and show fewer side effects such as gastric problems and allergies because of the absence of additions such as plasticizers. In addition, such liquid or semisolid formulations can be produced particularly easily.

DETAILED DESCRIPTION OF THE INVENTION

1. Preferred Aspects of the Invention

Figure 1:
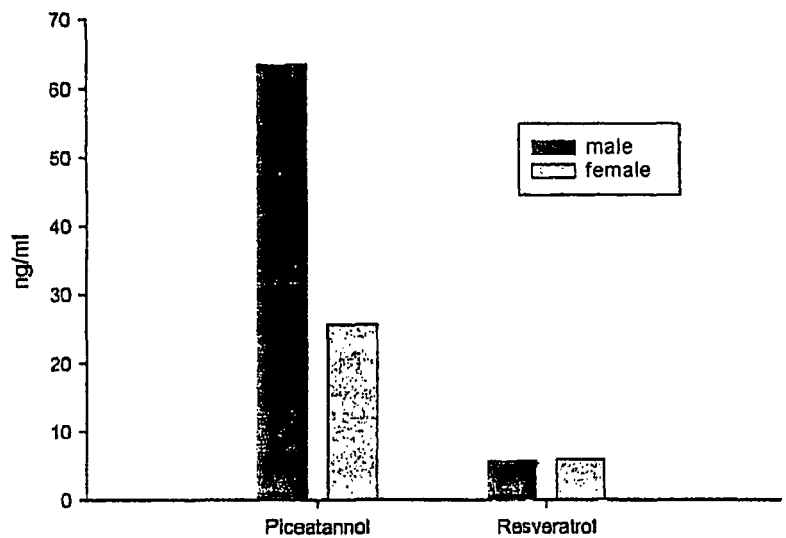
FIG. 1 shows the formulation of piceatannol and resveratrol in vivo in male and female dogs 24 hours after administration of 100 mg of ERr 731/kg of body weight.

The invention relates to a solid dosage form, comprising an active ingredient-containing solid core with a pharmaceutically acceptable carrier and an active ingredient content of about 1 to 20% by weight, based on the total weight of the core, where the active ingredient is a hydroxystilbene-containing active ingredient or a hydroxystilbene-containing active ingredient combination, selected from prodrugs of resveratrol and piceatannol (precursors), such as, in particular, rhaponticin, deoxyrhaponticin, cis- and trans-rhapontigenin, deoxyrhapontigenin and astringin; and resveratrol and piceatannol; and the stereoisomeric forms thereof, in each case in the form of their salts or in the phenol form and functional derivatives, and combinations of these compounds.

Resveratrol and piceatannol prodrugs in the sense of the invention are in particular substances which can be converted, partly or wholly, into resveratrol and/or piceatannol in vivo, such as, for example, in humans and/or another mammal, such as, for example, dog. Possibilities in this connection are sugar-containing (glycosides) or sugar-free (aglycones) natural or synthetic precursors of resveratrol or piceatannol. Typical examples of sugar-containing precursors include rhaponticin, astringin and deoxyrhaponticin. Typical examples of sugar-free precursors include rhapontigenin and deoxyrhapontigenin. The terms "prodrug" or "precursor" are, however, not to be understood as functional restriction in the context of the invention. As proven by the experimental results described hereinafter, in particular the "precursors" of the invention per se display advantageous pharmacological effects.

The active ingredients are preferably substantially present in the trans form. Salts are in particular the alkali metal and alkaline earth metal phenolates of the above compounds which have one or more free phenolic hydroxyl groups. If a plurality of hydroxyl groups is present, these can be partly or completely in the salt form.

The active ingredient to be employed according to the invention or the active ingredient combination is in this connection chemically synthesized or, in particular, is an ingredient which can be isolated from natural or recombinant plants or an ingredient combination which can be isolated therefrom and contains at least one of the abovementioned hydroxystilbene compounds. The resulting plant extracts or individual components thereof can also be subjected to derivatization reactions in order to obtain so-called functional derivatives. These are in particular derivatives which can be converted back in the human or animal body, after administration, into the underivatized starting compound again. Mention should be made in particular of ethers and ester derivatives of the compounds used according to the invention. It is moreover possible for individual ones or all of the etherifiable or esterifiable groups in a molecule (especially the phenolic and glucosidic hydroxy groups) to be derivatized. Examples of suitable derivatives and their preparation are described for example in FR 2 835 185, which is incorporated herein by reference. Thus, mention may be made of: esters of saturated or unsaturated, aliphatic or aromatic carboxylic acids having up to 25 carbon atoms, such as 1 to 25 carbon atoms, such as, for example, saturated $C_6$-$C_{22}$ fatty acids (such as, for example, saturated unbranched fatty acids selected from caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid); or silyl ethers, where the silicon atom carries three identical or different, straight-chain or branched, saturated or unsaturated hydrocarbon radicals having up to 20 carbon atoms, such as, for example, $C_1$-$C_{20}$ alkyl or $C_2$-$C_{20}$ alkenyl.

An active ingredient combination of at least two of the abovementioned compounds is preferably employed, such as, for example, 2, 3, 4, 5, 6, 7 or 8 individual compounds, where the group of resveratrol precursors (especially deoxyrhaponticin and deoxyrhapontigenin) and of piceatannol precursors (especially rhaponticin and rhapontigenin) is represented in each case by one compound.

In a preferred embodiment, the active ingredient or the active ingredient combination is obtainable from plants which are selected from natural plants and plants which have been modified by breeding or recombinant, genetically modified plants, which have a content of at least one of the desired ingredients which is higher by comparison with the corresponding unmodified plant. These plants are in particular selected from plant of the genus *Rheum* spp., *Astragalus* spp., *Cassia* spp. or *Picea* spp. or active ingredient-containing plant parts. Nonlimiting examples of suitable species of these genera are *Rheum undulatum, Rheum palmatum, Rheum tataricum, Rheum officinale, Rheum wittrockii, Rheum altaicum, Rheum reticulatum, Astragalus complanatus, Cassia garrettiana* and *Picea sitchensis*.

The skilled person is additionally aware that genera/species differing in provenance and differing in age (e.g. harvest at various times of the vegetation period) can be employed, in turn possibly influencing the nature, amount and composition of the active ingredients and mixtures which can be isolated therefrom. It is likewise possible in principle to use various plant parts, such as roots, rhizomes, leaves and/or stalks.

The active ingredient or the active ingredient combination is particularly advantageously obtainable from the roots and/or other plant parts, especially of *Rheum rhaponticum*.

In a further embodiment, the active ingredient combination substantially comprises rhaponticin and deoxyrhaponticin, it being possible for the active ingredient combination in particular substantially to comprise rhaponticin and deoxyrhaponticin in a ratio by weight of about 10:1 to 1:10, such as, for example, in a range of about 5:1 to 1:5 or 4:1 to 1:4 or 3:1 to 1:3 or 2:1 to 1:2 or about 1:1.

In a specific dosage form the active ingredient combination of substantially rhaponticin and deoxyrhaponticin is present in a ratio by weight of about 2:1 to 1:2.

A further preferred active ingredient combination may comprise rhaponticin and deoxyrhaponticin, in particular in the ratios of amounts indicated above, and rhapontigenin and/or deoxyrhapontigenin. The quantitative proportion of rhapontigenin and/or deoxyrhapontigenin in the total active ingredient content may vary over a wide range and is, for example, in the range of about 0.01 to 20% by weight, in particular 0.1 to 5% by weight, based on the total active ingredient content.

Preference is further given to active ingredient combinations which have a total hydroxystilbene content, in particular a total content of deoxyrhaponticin, deoxyrhapontigenin, rhaponticin and rhapontigenin, or a total content of rhaponticin and deoxyrhaponticin, of more than 90% by weight, such as, for example, 91 to 100% by weight, or 92 to 99 or 93 to 98 or 94 to 97% by weight.

In a further preferred embodiment there is use of an active ingredient combination which is substantially free of aglycone derivatives of rhaponticin and deoxyrhaponticin, such as, in particular, resveratrol and piceatannol. "Substantially free" means an aglycone content of less than 5% by weight, in particular less than 2% by weight, such as, for example, less than 1% by weight or 0.1% by weight, such as 0 to 0.05% by weight, in each case based on the total content of rhaponticin plus deoxyrhaponticin.

In a further preferred embodiment an active ingredient combination used is a plant dry extract which has a high content of glycosides, in particular glycosides of the type described above. Glycosides are in particular the above-described glycosidic precursors of resveratrol and piceatannol. These are present for example in a content of from 30 to 100% by weight, 50 to 100% by weight, but preferably in contents of more than 76% by weight, such as 76 to 99% by weight or 80 to 98% by weight or 85 to 96% by weight, in each case based on the total weight of the dry extract.

Preference is further given to active ingredient combinations which have a content of less than 0.5% by weight, such as, for example, 0-0.49% by weight or 0.001 to 0.3 or 0.01 to 0.2 or 0.01 to 0.1% by weight of anthraquinone and/or anthraquinoids (in each case based on the dry weight of the active ingredient combination). Anthraquinoids are in this connection to be understood in the widest sense as substances having a basic anthraquinone structure.

A "dry extract" in the sense of the invention is one where the residual moisture content, i.e. the residual content of water and/or organic liquid (such as extractant), is less than about 5% by weight, in particular less than 2% by weight, such as, for example, 0 to 1.5% by weight or 0.1 to 0.5% by weight, in each case based on the total weight of the resulting dry extract.

Nonlimiting examples of suitable solid dosage forms are those where the active ingredient combination consists substantially of about 60-66% by weight rhaponticin
30-35% by weight deoxyrhaponticin
0-2% by weight rhapontigenin;
0-2% by weight deoxyrhapontigenin.

Preferred solid dosage forms have a total active ingredient content of about 2 to 20 mg per dose unit.

The invention relates in particular to solid dosage forms which have a sugar-free, in particular mono- or disaccharide-free, such as, for example, lactose-free, core.

Suitable solid dosage forms may be in the form of a pill, a tablet, an extrudate or granules.

Solid dosage forms in the form of a coated tablet, where appropriate with a gastro-resistant coating, are particularly preferred. Such coatings are preferably free of plasticizers such as phthalates, such as, for example, diethyl phthalate. Coating compositions suitable in particular for producing gastro-resistant, plasticizer-free coatings are selected from known natural and synthetic coating compositions (cf., for example, Voigt, Pharmazeutische Technologie, 7th edition 1993, Ullstein Mosby, Berlin). Particularly suitable coating compositions are, without being restricted thereto, shellac and cellulose derivatives such as hydroxypropylmethylcellulose derivatives such as, for example, hydroxypropylmethylcellulose acetate succinate, obtainable under the proprietary name AQOAT.

Mention should be made in particular of a solid dosage form with a total weight in the range of about 150 mg±20 mg, a core weight of 84 mg±10 mg and an active ingredient content of about 3 to 10 mg.

Further preferred solid dosage forms are those having a uniformity of active ingredient content (averaged over 10 or 20 randomly selected individual dose units) not exceeding ±5% by weight, such as, for example, ±0.1 to 4 or ±0.5 to 3 or ±1 to 2% by weight, based on the total weight of the dose unit (e.g. determined as specified in Ph. Eur. 5th edition 2005 (5.0/2.09.06.00)).

The invention further relates to a process for producing a solid dosage form where
a) the active ingredient or the active ingredient combination is mixed with the pharmaceutically acceptable carrier; and
b) the mixture is consolidated to give the active ingredient core.

For this purpose, the active ingredient or the active ingredient combination is preferably dissolved or dispersed in an inert liquid and mixed with the carrier, and the solvent is removed during or after the consolidation.

The active ingredient used according to the invention or the active ingredient combination is advantageously prepared by
a) providing an active ingredient-containing part of a medicinal plant, where appropriate in comminuted form,
b) adding an aqueous extractant thereto,
c) after the extractant has acted, obtaining a liquid extract phase from the mixture and, where appropriate, repeating the extraction several times, and
d) removing the extractant from the liquid extract phases obtained in this way.

This preferably entails carrying out an extraction with an aqueous extractant at a pH of the mixture in the alkaline range.

The extracted medicinal plant is selected in particular from plants of the genus *Rheum* spp, *Astragalus spp, Cassia* spp or *Picea* spp.

In a preferred variant of the preparation process, the total amount of the active ingredient or of the active ingredient combination is mixed in portions with the pharmaceutically acceptable carrier, such as, for example, Avicel or a comparable cellulose-based carrier, in particular microcrystalline cellulose, and the mixing process is repeated after each addition of carrier, but at least one or twice. In particular, a ball mill is used in this case for mixing over a period of from 30 minutes to 3 hours, such as, for example, 1 to 2 hours. It is possible to use for example conventional laboratory ball mills as described in the examples for the mixing. This results in a homogeneous and stable distribution of the active ingredient in the carrier.

In a further variant of the process, the active ingredient core is provided with a gastro-resistant, preferably plasticizer-free, coating.

In a further preferred variant in this connection, the core is sugar-coated.

The invention also relates to liquid dosage forms comprising an active ingredient or an active ingredient combination as defined above in a content of about 0.1 to 20 mg/ml, such as, for example, 0.5 to 15 or 1 to 10 or 2 to 5 mg/ml, in a solvent mixture comprising water and a pharmaceutically acceptable alcohol such as, in particular, ethanol. The solvent mixture is preferably a water/ethanol mixture with an ethanol content of from 10 to 50 or 20 to 40 or 25 to 35% by volume, such as, for example, 30% by volume. These liquid dosage forms are formulated in particular as drops for oral administration.

The invention also relates to semisolid dosage forms comprising an active ingredient or an active ingredient combination as defined above in a content of about 1 to 12, or 2 to 6, mg of active ingredient or active ingredient combination (per gram of the formulation) in a conventional semisolid carrier. Suitable gel-forming carriers are generally known and are selected for example from swellable cellulose derivatives such as hydroxypropylmethylcellulose, or polyacrylates such as, for example, carbopol, or gelatin. Dosage forms of this type can be used for example as vaginal gel or vaginal suppositories.

The invention also relates to a composition comprising a solid, semisolid or liquid dosage forms as defined above. Compositions in the sense of the invention are in particular pharmaceutical compositions or medicaments such as, for example, homeopathic remedies, and medicinal plant preparations.

A further aspect of the invention relates to the use of a solid, semisolid or liquid dosage form as defined above or prepared by one of the processes described above or producing a composition as defined above for the treatment of menopausal symptoms in women, especially for the treatment of menopausal symptoms in the pre- or postmenopause, and menopausal symptoms owing to a natural or therapeutically induced menopause. Menopausal symptoms are in this connection in particular hot flushes, sweaty episodes, sleep disorders, irritability, psychological and mental exhaustion, sexual problems and urinary tract symptoms. The invention also relates to their use for treating juvenile oligomenorrhea and dysmenorrhea, primary and secondary amenorrhea or endometritis.

Owing to the excellent tolerability of the active ingredients or active ingredient combinations described above, the invention also relates to the use during long-term therapy, which is possible without limitation in time. The daily dose to be administered in this connection can be in the range from 0.1 to 20 mg or 0.5 to 15 mg, 1 to 10 or 4 to 8 mg of active ingredient or active ingredient combination such as, for example, ERr 731®.

A treatment in the sense of the invention includes both an acute and a preventive administration of compositions of the invention.

Finally, the present invention also relates to the use of the active ingredients or active ingredient combinations described above, e.g. formulated in one of the dosage forms described above, for selective activation of ERβ, i.e. activation of ERβ without simultaneous substantial or detectable activation of ERα in vivo or in vitro.

The invention therefore relates in particular also to the use of an active ingredient or of an active ingredient combination as defined above (such as in particular of ERr 731 or similar combinations comprising rhaponticin and/or deoxyrhaponticin) for treating one of the disorder defined above by selective activation of ERβ, i.e. activation of ERβ without simultaneous substantial or detectable activation of ERα.

2. Further Specific Refinements of Formulations According to the Invention a) Dosage Forms The teaching of the invention is directed especially at the production of solid, semisolid or liquid dosage forms for treating a person. Thus, the active ingredients to be used according to the invention are usually administered in the form of pharmaceutical compositions which comprise a pharmaceutically acceptable excipient with at least one active ingredient of the invention and, where appropriate, further active ingredients. These compositions can be administered in particular by the oral route.

Examples of suitable pharmaceutical formulations are in particular solid pharmaceutical forms such as granules, tablets, pastilles, sachets, cachets, sugar-coated tablets and capsules such as hard and soft gelatin capsules, pessaries, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops, nose drops, nasal spray and tinctures. It is also possible to use implanted delivery devices for administering inhibitors of the invention. Liposomes, microspheres or polymer matrices can also be used in addition.

In the production of the compositions, active ingredients of the invention are usually mixed with an excipient or diluted. Excipients may be solid, or semisolid materials which serve as vehicle, carrier, adsorbent or medium for the active ingredient or the active ingredient combinations.

Examples of suitable excipients include, unless indicated otherwise, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose and methylcellulose. The formulations may in addition comprise usual pharmaceutically acceptable ancillary substances such as lubricants, for example tallow, magnesium stearate and mineral oil; wetting agents; emulsifying and suspending agents; preservatives such as methyl and propyl hydroxybenzoates; antioxidants; antiirritants; insulating agents; tablet-coating aids; emulsion stabilizers; film formers; gel fomers; odor-masking agents; taste correctives; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; tablet excipients such as binders, fillers, lubricants, disintegrants or coatings; propellants; dessicants; opacifiers; thickeners; waxes; plasticizers. An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996; cf. also Hager's Handbuch der Pharmazeutischen Praxis, Springer Verlag, Heidelberg.

Solvents which are suitable according to the invention for producing formulations and which should be particularly mentioned are monohydric or polyhydric alcohols such as, in particular, ethanol, glycerol and mixtures thereof with water, such as, for example 1 to 50% by volume ethanol in water.

Dosage forms or pharmaceutical compositions of the invention are produced by using generally known methods of pharmaceutical technology as described for example in Voigt, Pharmazeutische Technologie, 7th edition 1993, Ullstein Mosby, Berlin.

In a preferred embodiment, a pharmaceutical composition which comprises a solid dosage form is provided. This solid dosage form in turn includes an active ingredient-containing solid core with a pharmaceutically acceptable carrier and an active ingredient content of about 1 to 20% by weight, based on the total weight of the core, where the active ingredient is a hydroxystilbene-containing active ingredient or a hydroxystilbene-containing active ingredient combination which includes a compound selected from resveratrol and piceatannol prodrugs, such as rhaponticin, deoxyrhaponticin, rhapontigenin, deoxyrhapontigenin and astringin; and resveratrol and piceatannol; and the stereoisomeric forms thereof, in each case in the form of their salts or in the phenol form, or combinations of these compounds. Preferred active ingredient combinations are as defined above.

This solid dosage form has for example a total active ingredient content of about 1 to 20 mg, such as, for example, 2 to 10 mg, per dose unit and can be in the form of a pill, a tablet, an extrudate or granules, and for example be sugar-coated. If desired, it may also have a gastro-resistant coating.

The solid dosage form is produced for example by mixing the active ingredient or the active ingredient combination with the pharmaceutically acceptable carrier, and consolidating the mixture to give the active ingredient core. This entails dissolving or dispersing the active ingredient or the active ingredient combination in an inert liquid, mixing it with the carrier and removing the solvent during or after the consolidation. The active ingredient core can then be provided where appropriate with a gastro-resistant coating before the core is sugar-coated in a conventional way.

Liquid dosage forms of the invention are produced for example by dissolving the active ingredient(s) such as, for example, an ERr 731® dry extract in a suitable solvent such as, for example, a water/alcohol mixture, where appropriate together with further conventional additions.

Semisolid dosage forms of the invention, such as, for example, gels, are produced for example by dissolving the active ingredient(s), such as, for example, an ERr 731® dry extract, in a suitable solvent such as, for example, a water/alcohol mixture, alcohol or glycerol, and incorporating the solution into the previously swollen gel former, where appropriate together with further conventional additions.

The mode and duration of administration of the medicaments of the invention are subject to the decision of the treating physician. The latter can establish a suitable dose and an appropriate dosage regimen depending on the chosen route of administration, on the efficacy of the specific active ingredient composition, the nature and severity of the disorder to be treated, the patient's condition and his response to the therapy. For example, a suitable single dose may comprise about 0.1 to 50 mg, such as, for example, 2 to 12 mg, of active ingredient or active ingredient combination as defined above, and be administered 1 to 3 times a day until the desired result of the treatment is to be observed.

b) Preparation of a Drug Extract which can be Used According to the Invention

Drug extracts which can be used according to the invention are preferably prepared by
  a) providing a hydroxystilbene-containing part of a medicinal plant, where appropriate in comminuted form,
  b) adding an aqueous, organic or aqueous-organic extractant thereto,
  c) after the extractant has acted, obtaining a liquid extract phase from the mixture, and where appropriate repeating the extraction several times, and
  d) removing the extractant from the liquid extract phases obtained in this way.

In particular, the extract obtained in this way includes at least one compound selected from rhaponticin, deoxyrhaponticin, rhapontigenin, deoxyrhapontigenin as salt or in phenolic form, in a stereoisomeric form thereof, such as cis or trans form, or as mixture of such stereoisomeric forms.

However, the extracted hydroxystilbenes are preferably substantially in the trans form. Salts are in particular the alkali metal and alkaline earth metal phenolates of the above compounds which have one or more free phenolic hydroxyl groups. If a plurality of hydroxyl groups is present, they may be partly or completely in the salt form.

The resulting plant extracts or individual components thereof can, as already mentioned, also be subjected to derivatization reactions in order to obtain so-called functional derivatives.

An active ingredient combination of at least two of the abovementioned compounds is preferably obtained, such as, for example, 2, 3, 4, 5, 6, 7 or 8 individual compounds, with the group of resveratrol precursors (especially deoxyrhaponticin and deoxyrhapontigenin) and of piceatannol precursors (especially rhaponticin and rhapontigenin) each being represented by one compound.

A further preferred embodiment of the process of the invention provides an extract which has a high content of glycosides, in particular glycosides of the type described above, such as, for example, a content of from 30 to 100% by weight, 50 to 100% by weight, 60 to 99% by weight or 80 to 98% by weight or 85 to 96% by weight, in each case based on the total weight of the resulting dry extract. A "dry extract" in the sense of the invention is present in particular when the residual moisture content of water and/or organic liquid (such as extractant) is less than about 5% by weight, in particular less than 2% by weight, such as, for example, 0 to 1.5% by weight or 0.1 to 0.5% by weight, in each case based on the total weight of the resulting dry extract.

A further preferred embodiment provides an extract which is substantially free of aglycone derivatives of rhaponticin and deoxyrhaponticin, such as, in particular, resveratrol and piceatannol. "Substantially free" means an aglycone content of less than 5% by weight, in particular less than 2% by weight such as, for example, less than 1% by weight or 0.1% by weight, such as 0 to 0.05% by weight, in each case based on the total weight of rhaponticin and deoxyrhaponticin.

Active ingredient combinations which are further preferably prepared are those having a total hydroxystilbene content of more than 90% by weight such as, for example, 91 to 100% by weight, or 92 to 99 or 93 to 98 or 94 to 97% by weight.

Further active ingredient combinations which are preferably prepared are those having a content of less than 0.5% by weight, such as, for example, 0-0.49% by weight or 0.001 to 0.3 or 0.01 to 0.2 or 0.01 to 0.1% by weight, of anthraquinone and/or anthraquinoids (in each case based on the dry weight of the active ingredient combination). Anthraquinoids are in this case to be understood in the widest sense as substances having a basic anthraquinone structure.

In a preferred embodiment, the medicinal plant to be extracted is selected from natural plants and plants modified by breeding or recombinant, genetically modified plants which have a content of at least one of the desired ingredients which is higher by comparison with the corresponding unmodified plant. These plants are selected in particular from plants of the genus *Rheum* spp., *Astragalus* spp., *Cassia* spp. or *Picea* spp. or active ingredient-containing plant parts. Non-limiting examples of suitable species of these genera are *Rheum undulatum, Rheum palmatum, Rheum tataricum, Rheum officinale, Rheum wittrockii, Rheum altaicum, Rheum reticulatum, Astragalus complanatus, Cassia garrettiana* and *Picea sitchensis*. It is additionally preferred to employ medicinal plants as single varieties.

The skilled worker is additionally aware that genera/species differing in provenance and differing in age (i.e. harvest at various times of the vegetation period) can be employed, in turn possibly influencing the nature, amount and composition of the hydroxystilbenes and mixtures which can be isolated therefrom. It is likewise possible in principle to use various plant parts such as roots, rhizomes, leaves and/or stalks.

The respective plant part or mixture of plant parts can, if expedient, be mechanically treated such as, for example, ground, chopped, reeled, crushed or cut. If expedient, predrying is also possible, such as, for example, 2 hours to 2 days at 30 to 50° C., in order to reduce the liquid content.

The hydroxystilbene-containing part of the medicinal plant used for the extraction is in particular the root of the medicinal plant, such as, for example, of *Rheum rhaponticum*.

The invention relates in particular to a process in which a hydroxystilbene-containing percolate is prepared from the drug. A "percolation" means a continuous extraction of soluble substances from a drug by continual renewal of the solvent. This results in a permanent concentration gradient, so that a large part of all the soluble substances goes into the extract.

An alternative possibility is also a continuous or periodic mixing of the batch such as, for example, by stirring or shaking.

The temperature during the extraction according to the invention is usually in the range from 10 to 50° C., such as, for example, 25 to 35° C. The pressure is usually atmospheric pressure. If a speeding up of the rate of extraction or quality of the extract can be achieved, the pressure may also be varied during the extraction, such as, for example, raised or lowered.

The extraction may take, depending on the chosen conditions such as the nature of the drug, batch size, extractant and temperature used, from 1 hour to several days, such as, for example, 10 to 72 hours.

The extraction process can if necessary be repeated several times in order to ensure that isolation in particular of the desired ingredients is as complete as possible. The ratio by weight of introduced drug to liquid extractant may vary over a wide range and from extraction step to extraction step. The ratio by weight of drug to extractant is typically in the range from 10:1 to about 1:200 or about 1:2 to 1:50, or 1:4 to 1:10.

In one variant of the process, an extraction is carried out with an aqueous extractant which is substantially free of organic solvent, such as, in particular, water, preferably purified water, at a pH of the mixture in the alkaline range, with the pH of the mixture being in particular in the range from about 11 to 12, such as, for example, about 11.3 to 11.8.

The pH of the mixture is adjusted for example with the aid of an inorganic base selected from alkali metal and alkaline earth metal hydroxides such as, for example, calcium hydroxide or calcium oxide. It is possible for this purpose for example to prepare a concentrated quicklime solution by dissolving 3 to 8 parts of CaO in 20 parts of purified water. This solution is strongly alkaline and has a pH in the range from about 12 to 13, such as, for example, of about 12.4 to 12.6.

The ratio of the amounts of introduced drug to base such as, for example, calcium hydroxide (calculated as calcium oxide) can be according to the invention in the range from about 5:1 to 20:1, such as about 8:1 to 12:1 or 9:1 to 11:1.

The process is preferably carried out in such a way that the desired hydroxystilbenes are precipitated from the resulting alkaline liquid extract phase, for example by adjusting the pH of the extract to a value in the range from about 3 to 4, such as, for example, 3.2 to 3.8, or 3.4-3.6, and, where appropriate, subsequently removing the precipitate, washing where appropriate and drying where appropriate.

Used for the acidification is any inorganic or organic acid, such as, for example, hydrochloric acid or sulfuric acid, but in particular organic acids such as formic acid or acetic acid.

Before removal of the precipitate it may be expedient to leave the batch to stir for some hours or days in order to achieve precipitation which is as quantitative as possible of the desired extracted ingredients.

The precipitate can be washed for example with purified water, and this serves in particular to remove remaining acid.

Remaining liquid is removed from the extract by drying, e.g. at 30 to 50° C. or 35 to 45° C., for example over a period of from 1 to 100 hours, until the residual moisture is in the range indicated above. The drying takes place in a manner known per se, e.g. in a drying oven. Freeze drying is likewise possible.

The invention is now further explained by means of the following nonlimiting examples.

EXPERIMENTAL SECTION

General Methods:
Determination of Stilbenes by High-Pressure Liquid Chromatography (HPLC) in the Dry Extract from Rhapontic Rhubarb Root
a) Sample Preparation:

50 mg of extract, mixed with 40 ml of a mixture of acetone and water (1:1) in an amber glass vessel, treated in an ultrasonic bath for 15 minutes and made up to 50 ml with the solvent mixture and then diluted 1:10 with the solvent mixture.

b) Procedure for the Chromatography:

A high-pressure liquid chromatography (HPLC) is carried out on a portion of the solution obtained above, with the following system parameters:

| Sample loop: | 20 μl |
|---|---|
| Column: | Lichrospher 5μ RP 18, 250 × 4 mm |
| Precolumn: | Lichrospher 5μ RP 18, 5 × 4 mm |
| Column temperature: | 25° C. |
| Eluent A: | Acetonitrile/dist. water/phosphoric acid 85%, 15/85/0.05 (parts by volume) |
| Eluent B: | Acetonitrile/dist. water/phosphoric acid 85%, 80/20/0.05 (parts by volume) |
| Flow rate: | 1.5 ml/min |
| Column flushing: | 15 min with eluent 50% B; equilibration time 15 min |
| Detection: | 310 nm |
| HPLC: | Kontron Kroma 2000 |

| Gradient: | |
|---|---|
| Time | % B |
| 0.0 | 0 |
| 0.5 | 0 |
| 7.5 | 75 |
| 8.5 | 100 |
| 9.5 | 0 |
| 12.5 | 0 |

The retention times resulting under the system conditions indicated above are as follows:

| Rhaponticin: | about 5.5 min |
|---|---|
| Deoxyrhaponticin: | about 6.8 min |
| Rhapontigenin: | about 7.2 min |
| Deoxyrhapontigenin: | about 9.0 min |

For a quantitative determination, the respective peak areas are found and compared with the corresponding peak areas of a standard extract of known composition.

Preparation Example 1

Preparation of the Dry Extract ERr 731 from Rhapontic Rhubarb Root with an Aqueous Calcium Hydroxide Solution A dry extract is prepared from rhapontic rhubarb root employing the following:

| Drug (radix rheum rhaponticum) | 50.0 kg |
|---|---|
| Calcium oxide | 5.0 kg |
| Purified water | 190.0 kg |
| Acetic acid (as necessary to adjust the required pH) | |

The yield which can be achieved in this case is between 2 and 3 kg per 50 kg of drug.

The preparation takes place in the following steps:
a) Firstly 5 kg of calcium oxide are introduced into a plastic tub and made into a slurry with 20 kg of purified water. The formation of calcium hydroxide (quicklime) which takes place under these conditions leads to a large rise in temperature of the solution. The calcium hydroxide can therefore be used further only after cooling. The temperature of the solution is then 30° C. to 35° C.
b) 50 kg of drug are introduced into a mixer, and the above-mentioned quicklime is added. In order to remove the quicklime as completely as possible from the plastic tub, it is rinsed with 10 kg of purified water. This washing liquid is likewise put in the mixer.
c) The drug homogeneously mixed with quicklime is introduced into a percolator and covered with 160 kg of purified water. The percolator remains closed for 48 hours. The percolate is then collected in a suitable vessel at a flow rate of 50 ml/min. The percolation is continued until no further percolate emerges. The drug mass is not squeezed out after completion, but is discarded.
d) While monitoring continuously, concentrated acetic acid is added to the percolate until a pH in the range from 3.4 to 3.6 is reached. In order to achieve precipitation of the extract which is as complete as possible, the mixture is left to stand for 5 days.
e) The dry extract is obtained by filtration through Büchner funnels under applied vacuum. Finally, the extract is washed with 10 to 20 kg of purified water.
f) The dry extract obtained after filtration is dried in a drying oven at 40° C. until a residual moisture tolerance not exceeding 1% is reached.

Rhaponticin is readily soluble in aqueous solutions with an alkaline pH range, whereas it is precipitated as yellowish substance in the acidic pH range (pH 3.4-3.6). Use is made of this for its isolation. Since, besides other organic acids, the root in particular has a high content of oxalic acid (⅔ in water-soluble and ⅓ in bound form), this must be neutralized during the isolation in order to prevent the pH drifting into the acidic range and thus to inhibit premature precipitation of the rhaponticin. This is achieved by using calcium oxide. The latter is employed as quicklime solution with a pH of 12.4-12.6.

Homogeneous mixing of the quicklime with the drug alters the pH of the mixture. It is then in the range from 11.3 to 11.8, thus preventing precipitation of rhaponticin, because the phenolic form has been converted into a phenolate form. Despite the high oxalic acid content, the pH can be kept in the alkaline range. This is attributable to the fact that the calcium hydroxide reacts with oxalic acid and forms insoluble and nontoxic calcium oxalate.

Rhaponticin is extracted from the root by the subsequent percolation with purified water. After completion of the percolation, a pH of 3.4 to 3.6 is adjusted by adding acetic acid. This pH shift from the alkaline to the acidic range leads to a precipitation of rhaponticin through conversion back into the phenolic form. In order to achieve precipitation of rhaponticin which is as complete as possible, the mixture is left to stand for 5 days. It is then filtered. Rhaponticin remains as yellowish substance on the filter. The above statements about rhaponticin apply correspondingly to the other hydroxystilbene active ingredients isolated according to the invention.

Preparation Example 2

Preparation of a Dry Extract from Rhapontic Rhubarb Root with Various Organic Solvents The constituents mainly detectable in the rhapontic rhubarb root used as drug here belong to the group of hydroxystilbenes. Present from this group in the roots are rhaponticin (Rh) with a content of about 6% and deoxyrhaponticin (DRh) with a content of about 4%.

It is possible by exposure to the solvent systems indicated below, in a 100-fold quantity at room temperature for 10 minutes with shaking or stirring, to extract the proportions summarized below:

| Ethanol 86% | Rh  | 100.8% |
|---|---|---|
|             | DRh | 99.5%  |
| Ethanol 15% | Rh  | 77.1%  |
|             | DRh | 75.5%  |
| Acetone     | Rh  | 88.3%  |
|             | DRh | 96.6%  |
| Water, alkaline (pH 11, adjusted with CaO solution) | Rh | 75.5% |
|             | DRh | 60.5%  |

No useful results were achieved with heptane.

The respective yields of crude extracts in proportions by mass (based on drug employed) are as follows:

| Ethanol 86%     | 35.5% |
|---|---|
| Ethanol 15%     | 32.2% |
| Acetone         | 21.4% |
| Heptane         | 0%    |
| Water, alkaline | 4.5%  |

Extraction of rhapontic rhubarb root with ethanol-water mixtures leads to an extract which, besides the main constituents rhaponticin (about 30%) and deoxyrhaponticin (about 22%), comprises a further stilbene, which has not as yet been investigated, in a proportion of about 20% in the extract. Besides these, the aglycones rhapontigenin (about 8%) and deoxyrhapontigenin (about 2%) and a further 9 compounds which total about 20% are obtained.

The results on extraction with acetone are fundamentally the same.

Extraction with alkaline water (cf. conditions in preparation example 1) leads to an extract of greater purity.

The main constituents rhaponticin and deoxyrhaponticin are present in a proportion of about 97% in the dry extract. Rhapontigenin and deoxyrhapontigenin together amount to a proportion of 1.1% of the extract, whereas the stilbene which has not yet been investigated is present in a proportion of only 0.2%. A further 3 compounds are present in a proportion of 2.5%.

Formulation Example 1

Production of a Solid Dosage Form—Minitablet

1. Production of the Tablet Core:

A solid tablet core is produced using the following active ingredients and ancillary substances in the stated ratios of amounts (P=parts by weight). The ingredients are mixed and tabletted in three different ways:

a) Tablet Core Formulation:

| Purified dry extract according to preparation example 1 from rhapontic rhubarb root (ERr 731 ®) | 3.6 P |
|---|---|
| Microcrystalline cellulose (e.g. Avicel ®) | 57.0 P (±40%) |
| Sorbitol | 8.0 P (±40%) |
| Talc | 2.5 P (±40%) |
| Makrogol 6000 (polyglycol) | 1.6 P (±40%) |
| Polyvidone (K value about 25, e.g. Kollidon ® 25) | 1.6 P (±40%) |
| Sodium dodecyl sulfate (e.g. Texapon ® K 12) | 0.5 P (±40%) |
| Magnesium stearate (vegetable) | 0.8 P (±40%) |
|  | 75.6 P (±40%) |

It is possible by varying the weighed amount of ERr 731® and/or varying the amount of microcrystalline cellulose to obtain any desired ERr 731® contents in the untreated core (such as, for example, 2, 4, 6, 8, 10, 12 mg per tablet).

b) Mixing of Drug and Carrier

Mixing Variant a:

1.2 P of ERr 731® are triturated in portions with Avicel® in a ball mill and then, after addition of the other ancillary substances, mixed and tabletted as described below.

Mixing Variant b:

ERr 731® (1 g/l of solvent) is dissolved in a suitable solvent (e.g. ethanol/water mixture 86% v/v ethanol) and adsorbed on Avicel®, dried (at 40° C. for at least 48 hours) and, after addition of the other ancillary substances, mixed and tabletted as described below.

Mixing Variant c:

The total amount of Avicel® is divided into three equal portions. The first portion is mixed with the total amount of ERr 731® and triturated in a laboratory ball mill (e.g. type 1-25 LK, Alpine, Augsburg) for at least 120 minutes. The second portion of Avicel® is then added, and the mixture is again triturated in the laboratory ball mill for at least 120 minutes. After addition of the third portion of Avicel®, brief mixing is again carried out. Subsequently, after addition of the other ancillary substances, mixing and tabletting are carried out as described below.

It is surprisingly possible with this mixing variant to reduce markedly the tendency to inhomogeneity and, even with small dose units, to adjust an extremely uniform active ingredient content of not more than ±5% by weight (determined according to Ph. Eur. 5th edition 2005 (5.0/2.09.06.00)).

c) Tabletting:

The mixture of Avicel® and active ingredient is sieved through a sieving machine (sieve diameter 1.2 mm) into a suitable mixing container and, after addition of the stated tabletting aids (without magnesium stearate), mixed in a suitable mixer (e.g. drum hoop mixer of type Standard RR M 200, from Engelsmann AG/Ludwigshafen) for at least 30 min. Addition of magnesium stearate is followed by mixing again for at least 5 min.

The compression takes place in a suitable tablet press (e.g. rotary of type Perfecta Fette 2000, from Fette/Schwarzenbeck):

| | |
|---|---|
| Core weight: | 84 mg ± 4.2 mg maximum variation |
| Punch: | 7 mm diameter, domed |

The ERr-731 content per core is about 4 mg±5%.

2. Production of the Gastro-Resistant Coated Tablet

After removal of dust from the tablet cores with Eudragit, a gastro-resistant coating of cellulose acetate phthalate and diethyl phthalate, dissolved in isopropanol and ethyl acetate, is applied to the tablet cores using a coating system.

Macrogol is dissolved in purified water. The ingredients sugar (sucrose or isomalt), calcium carbonate, talc, titanium dioxide and the two povidones are mixed and stirred into the liquid. The suspension is stirred in a jet flow mixer (e.g. Rototron of type RTA 70-50) for 20 minutes.

The sugar-coating suspension is applied to the sealed core with the aid of an automatic coater. The process is repeated until an average weight of 150 mg per coated core is reached. Finally, the polishing wax is applied and then rolling is continued until a high gloss is obtained.

Final weight of the gastro-resistant coated tablet:
150 mg±7.5 mg maximum variation.

In this way, two different tablet forms—one containing sugar and one sugar-free—are produced, employing the respective ancillary substances in the parts by weight indicated below.

a) Gastro-Resistant Coated Minitablet—Containing Sugar—with Plasticizer in the Coating
Ancillary Substances:

| | | |
|---|---|---|
| Coating: | Eudragit L 12.5% dry matter | 1.350 kg (±40%) |
| | Diethyl phthalate | 1.749 kg (±40%) |
| | Cellulose acetate phthalate | 7.770 kg (±40%) |
| | Isopropyl alcohol | 75.600 kg (±40%) |
| | Ethyl acetate | 77.600 kg (±40%) |
| | Talc | 2.000 kg (±40%) |
| Sugar coating: | Talc | 7.182 kg (±40%) |
| | Sugar | 28.747 kg (±40%) |
| | Calcium carbonate | 6.410 kg (±40%) |
| | Titanium dioxide E 171 | 0.635 kg (±40%) |
| | Povidone | 0.756 kg (±40%) |
| | (K value about 25, e.g. Kollidon ® 25) | |
| | Povidone (K value about 90) | 0.332 kg (±40%) |
| | Macrogol 35,000 | 0.635 kg (±40%) |
| | Water | 10.500 kg (±40%) |
| Polish: | 95% carnauba wax, 5% bleached wax (e.g. Capol 1295 PH) | 0.108 kg (±40%) | b) Gastro-Resistant Coated Minitablet—Sugar-Free—with Plasticizer in the Coating
Ancillary Substances:

| | | |
|---|---|---|
| Coating: | Eudragit L 12.5% dry matter | 1.350 kg (±40%) |
| | Diethyl phthalate | 1.749 kg (±40%) |
| | Cellulose acetate phthalate | 7.770 kg (±40%) |
| | Isopropyl alcohol | 75.600 kg (±40%) |
| | Ethyl acetate | 77.600 kg (±40%) |
| Sugar coating: | Talc | 7.482 kg (±40%) |
| | Sorbitol and/or isomalt | 28.747 kg (±40%) |
| | Calcium carbonate | 6.410 kg (±40%) |
| | Titanium dioxide E 171 | 0.635 kg (±40%) |
| | Povidone | 0.756 kg (±40%) |
| | (K value about 25, e.g. Kollidon ® 25) | |
| | Povidone (K value about 90) | 0.332 kg (±40%) |
| | Macrogol 35,000 | 0.635 kg (±40%) |
| | Water | 10.500 kg (±40%) |
| Polish: | 95% carnauba wax, 5% bleached wax (e.g. Capol 1295 PH) | 0.108 kg (±40%) |

Formulation Example 2

Production of a Solid Dosage Form—Minitablet Containing Sugar without Plasticizer a) Production of the Tablet Core Production takes place in analogy to formulation example 1.

a) Production of the Gastro-Resistant Coated Tablet

Production takes place in analogy to formulation example 1, but with use of shellac (variant A) or Aqoat (variant B) instead of cellulose acetate phthalate/diethyl phthalate (plasticizer).

| a) Variant A | | |
|---|---|---|
| Ancillary substances: | | kg (±40%) |
| Coating: | Eudragit L 12.5% dry matter | 0.400 |
| | CAPOL 5270 PH 8% | 60.000 |
| | (shellac solution) = 4.8 kg | |
| | dry matter (shellac) | |
| | Isopropyl alcohol | 4.000 |
| | Ethanol 96% | 3.200 |
| | Talc | 2.000 |
| Sugar coating: | Talc | 7.182 |
| | Sugar | 28.747 |
| | Calcium carbonate | 6.410 |
| | Titanium dioxide E 171 | 0.635 |
| | Polyvidone | 0.756 |
| | (K value about 25, e.g. Kollidon ® 25) | |
| | Povidone (K value: about 90) | 0.332 |
| | Macrogol 35,000 | 0.635 |
| | Water | 10.500 |
| Polish: | 95% carnauba wax 5% bleached wax (e.g. Capol 1295 PH) | 0.108 | a) Variant B

| Ancillary substances: | | kg (±40%) |
|---|---|---|
| Coating: | Eudragit L 12.5% dry matter | 0.400 |
| | Aqoat | 5.420 |
| | Hydroxypropylmethylcellulose acetate succinate | |
| | Distilled water | 12.500 |
| | Isopropyl alcohol | 4.000 |
| | Ethanol 86% | 55.000 |
| Sugar coating: | Talc | 9.182 |
| | Sugar | 28.747 |
| | Calcium carbonate | 6.410 |
| | Titanium oxide E 171 | 0.635 |
| | Polyvidone | 0.756 |
| | (K value about 25, e.g. Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |

Formulation Example 3

Production of a Solid Dosage Form—Minitablet Sugar-Free without Plasticizer a) Production of the Tablet Core Production takes place in analogy to formulation example 1, but using isomalt instead of Avicel.

a) Production of the Gastro-Resistant Coated Tablet

Production takes place in analogy to formulation example 2, but using isomalt instead of sugar.

a) Variant A

| Ancillary substances: | | kg (±40%) |
|---|---|---|
| Coating: | Eudragit L 12.5% dry matter | 0.400 |
| | CAPOL 5270 PH 8% | 60.000 |
| | (shellac solution) = 4.8 kg | |
| | dry matter (shellac) | |
| | Isopropyl alcohol | 4.000 |
| | Ethanol 96% | 3.200 |
| | Talc | 2.000 |
| Sugar coating: | Talc | 7.182 |
| | Isomalt | 28.747 |
| | Calcium carbonate | 6.410 |
| | Titanium oxide E 171 | 0.635 |
| | Polyvidone | 0.756 |
| | (K value about 25, e.g. Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | | b) Variant B

| Ancillary substances: | | kg (±40%) |
|---|---|---|
| Coating: | Eudragit L 12.5% dry matter | 0.400 |
| | Aqoat | 5.420 |
| | Distilled water | 12.500 |
| | Isopropyl alcohol | 4.000 |
| | Ethanol 86% | 55.000 |
| | Talc | 2.000 |
| Sugar coating: | Talc | 7.182 |
| | Isomalt | 28.747 |
| | Calcium carbonate | 6.410 |
| | Titanium oxide E 171 | 0.635 |
| | Polyvidone | 0.756 |
| | (K value about 25, e.g. Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |

Formulation Example 4

Production of a Semisolid Dosage Form—Vaginal Gel

Production takes place using conventional methods by the two following variants:

a) Variant A:

Hydroxypropylmethylcellulose (hypromellose USP) or another gel former is allowed to swell with 2-10% by weight in purified water. The ERr 7310 (preparation example 1), dissolved in glycerol, is then incorporated. The amount of glycerol may be up to 50% of the weight of the gel. ERr 731® can be dissolved up to 0.5% by weight in glycerol. If necessary, preservatives (e.g. sorbic acid and its salts) can be added to the gel. Adjustment of the pH is also possible. As alternative to glycerol it is also possible to use 30-86% by volume ethanol.

b) Variant B:

Carbomer (Carbopol) is dissolved with 0.5-5% by weight in purified water, and the desired pH is adjusted (e.g. KOH, NaOH, NH$_3$). If necessary, a preservative (e.g. sorbic acid and its salts) is admixed. After formation of a clear gel, ERr 731® (preparation example 1) is dissolved up to 0.5% by weight in 30-86% by volume ethanol and added. As alternative to ethanol, it is also possible to use glycerol.

Formulation Example 5

Production of a Semisolid Dosage Form—Vaginal Suppositories

Suppositories with a size of 1 to 15 g with a content of 1 to 12 mg of ERr 731® (preparation example 1) dissolved in glycerol (85% n 20/D=1.45085) are produced in a conventional way by two different variants.

a) Variant A:

Formulation:

| Gelatin | 1 part |
|---|---|
| Purified water | 2 parts |
| Glycerol 85% (+ERr 731 ®) | 5 parts | b) Variant B:

Same formulation but with suitable preservatives such as, for example, sorbate, benzoate, PHB ester.

The gelatin is introduced in each case into purified water and allowed to swell until the mixture has become glassy. Glycerol 85% with active ingredient is then added and heated, but not above 65° C. The suppositories are then cast in a conventional way.

Formulation Example 6

Production of a Liquid Dosage Form—Drops a) Dissolving Tests with ERr 731® in Ethanol and Glycerol: Content of the extract:

| | |
|---|---|
| 61.9% rhaponticin | |
| 29.9% deoxyrhaponticin | |

Test A: 200 mg of dry extract in 50 ml of glycerol R:

| | |
|---|---|
| 55.1% rhaponticin | (89.0% of theory) |
| 27.1% deoxyrhaponticin | (90.6% of theory) |

Test B: 200 mg of dry extract in 50 ml of ethanol 30% R:

| | |
|---|---|
| 52.2% rhaponticin | (84.3% of theory) |
| 25.2% deoxyrhaponticin | (84.2% of theory) |

Test C: 200 mg of dry extract in 50 ml of ethanol 50% R:

| | |
|---|---|
| 58.8% rhaponticin | (95.0% of theory) |
| 29.0% deoxyrhaponticin | (97.0% of theory) |

Test D: 200 mg of dry extract in 50 ml of ethanol 86% R:

| | |
|---|---|
| 59.8% rhaponticin | (96.6% of theory) |
| 29.5% deoxyrhaponticin | (98.7% of theory) | b) Production of Drops:

Drops are produced by dissolving dry extract according to test B in ethanol 30% R and filtering where appropriate.

Test Example 1

IN Vivo Metabolism of the Dry Extract ERr 731®

For further elucidation of the mode of action, ERr 731® was administered orally by capsule to 3 male and 3 female dogs (pure-bred beagles, weight 6-9 kg, age 6-8 months) in a dose of 100 mg of ERr 731®/kg of body weight. At various time intervals, blood was taken from the animals and blood plasma was obtained. The plasma was investigated for ERr 731® ingredients and metabolites. It was surprisingly possible to detect both in male and in female animals significant amounts of the metabolite piceatannol and small amounts of the metabolite resveratrol. Maximum plasma levels of these metabolites were reached after about 24 h. The plasma levels of piceatannol were distinctly higher than those of resveratrol. The results of the test at the 24 h timepoint are depicted in FIG. 1.

Test Example 2

Investigation of the Activation of the Estrogen Receptor ERα by ERr 731® and the Ingredients or Metabolites Thereof It was intended to answer the question of whether ERr 731® activates ERα. The extract ERr 731® and the ingredients or metabolites thereof (trans-rhapontigenin, deoxyrhapontigenin, resveratrol, piceatannol and cis-rhapontigenin) were therefore investigated, comparing with 17β-estradiol, for the estrogenic activity in established model systems.

Test A):

In a first series of experiments, a recombinant yeast screen was used (cf. E. Routledge and J. P. Sumpter, Östrogenic activity of surfactants and some of their degradation products assessed using a recombinant yeast screen, Envirom. Tox. Chem. 1996).

*Saccharomyces cerevisiae* cells were stably transfected with human ERα both with a reporter gene consisting of the respective responsive promoter element fused to the LacZ gene which codes for β-galactosidase. Estrogen treatment (with estrogen or with a substrate having an estrogen-like effect) of the cells activates, mediated by the estrogen receptor, β-galactosidase, leading to a red coloration of the yeast cells, which can be measured at 565 nm.

Figure 2:
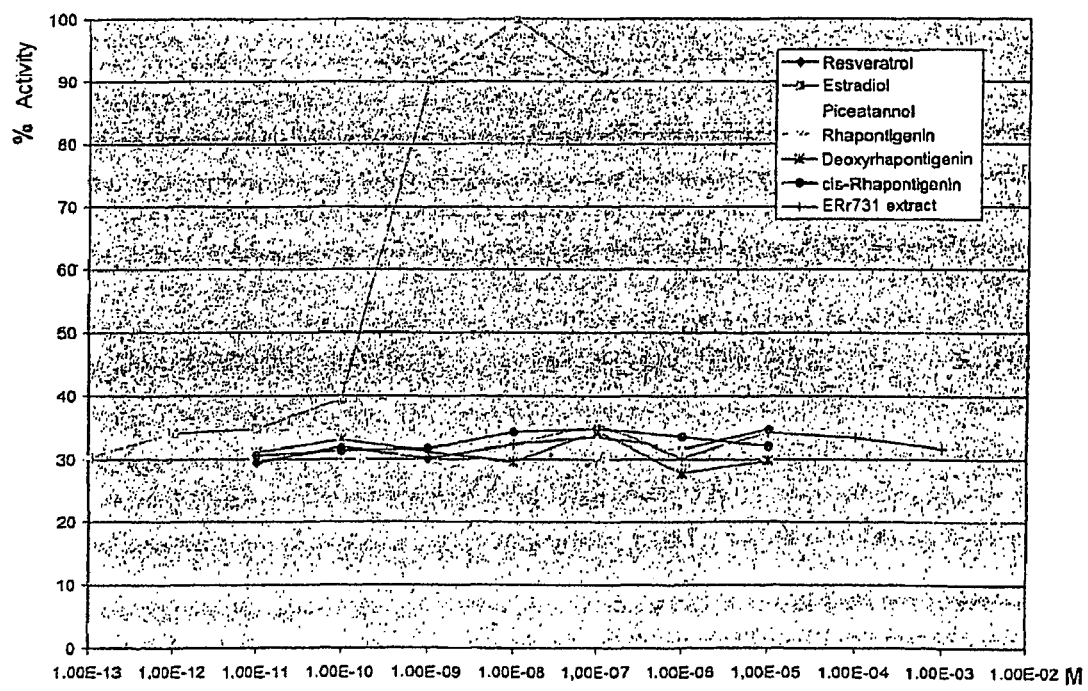
FIG. 2 shows the estrogenic activity of 17β-estradiol compared with resveratrol, cis- and trans-rhapontigenin, deoxyrhapontigenin, piceatannol and ERr 731® in a recombinant yeast screen stably expressing ER-α. The concentrations (X axis) are molar concentrations with the exception of the ERr 731® concentration, which is indicated in µg/ml.

The test results are summarized in FIG. 2.

Test B):

In a second series of experiments, the data of the estrogenicity measurement were verified by determining the induction of alkaline phosphatase in Ishikawa cells (human endometrial adenocarcinoma cells) which had been transfected with an ERα-containing reporter gene construct. The activity of alkaline phosphatase, which is assessed using the chromogenic substrate 4-nitrophenyl phosphate, represents an ERα-mediated response.

The test is based on the description by Holinka C F, Hata H, Kuramoto H, Gurpide E (1986) Effects of steroid hormones and antisteroids on alkaline phosphatase activity in human endometrial cancer cells (Ishikawa Line). Cancer Res. 46: 2771-2774, and modifications described in Wober J, Weißwange I, Vollmer G (2002) Stimulation of alkaline phosphatase activity in Ishikawa cells induced by various phytoestrogens and synthetic estrogens. J. Steroid Biochem. Mol. Biol. 83:227-233.

Table 2 presents the concentrations for the positive control (17β-estradiol) and the test substances used in the assay.

TABLE 2

| Test substance | Concentration (M)[1] |
|---|---|
| Estradiol | $10^{-6}$ |
| Resveratrol | $10^{-8}$-$10^{-5}$ |
| trans-Rhapontigenin | $10^{-8}$-$10^{-5}$ |
| Deoxyrhapontigenin | $10^{-8}$-$10^{-5}$ |
| Piceatannol | $10^{-7}$-$10^{-5}$ |

TABLE 2-continued

| Test substance | Concentration (M)[1] |
|---|---|
| cis-Rhapontigenin | $10^{-8}\text{-}10^{-5}$ |
| Extract ERr 731 ® | 0.00001-10 |

[1]Exception: The concentration for the extract ERr 731 is indicated in µg/ml

Figure 3:
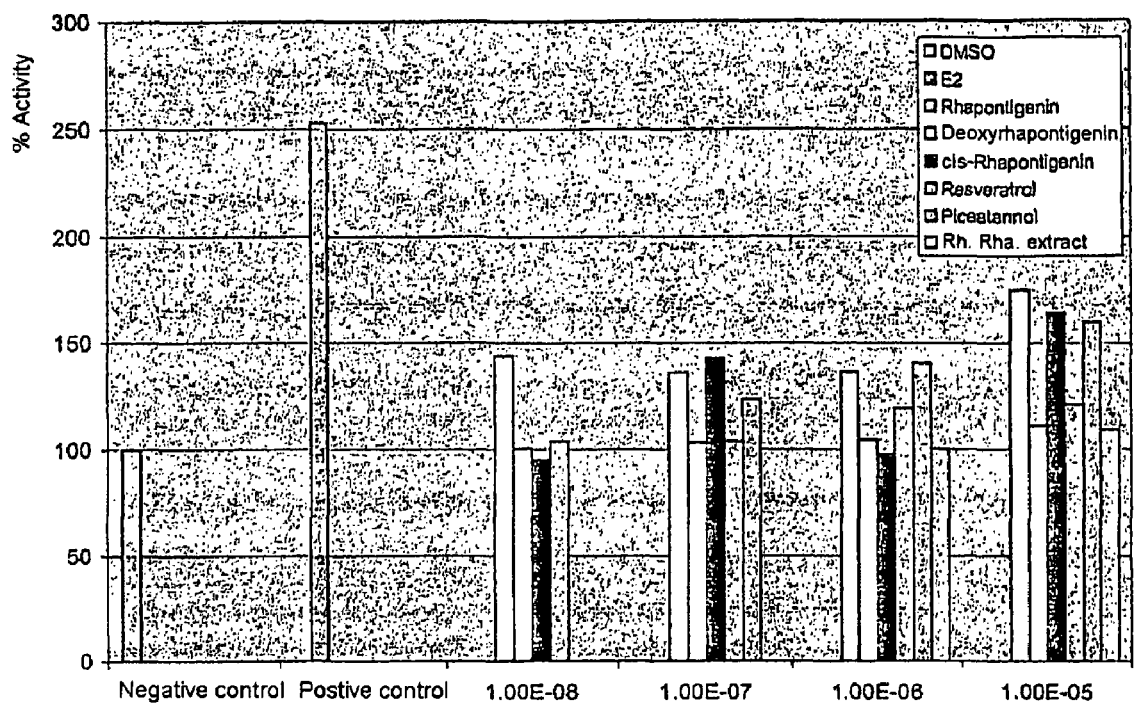
FIG. 3 shows the estrogenic activity of 17β-estradiol compared with resveratrol, cis- and trans-rhapontigenin, deoxyrhapontigenin, piceatannol and ERr 731®, indicated as activity of alkaline phosphatase in ishikawa cells transiently with ER-α. The concentrations (X axis) are molar concentrations with the exception of ERr 731® concentration, which is indicated in µg/ml.

The results of test B) are depicted in FIG. 3.

Both tests are conclusive because all the positive and negative controls show their predicted effects (cf. FIGS. 2 and 3). The results of the two test systems described above demonstrate that neither ERr 731® nor its ingredients and metabolites have a significant effect on the activation of ERα (cf. FIGS. 2 and 3). It can thus be assumed that the activity of ERr 731® is based on a molecular mechanism independent of ERα.

Test Example 3

Pharmacokinetics of ERr 731® Ingredients in Female Subjects

The intention was to check whether, after oral intake of ERr 731®, one of the ingredients of this active ingredient combination can be found again in the blood, in order to demonstrate that at least one of the constituents of this active ingredient combination or its metabolites is bioavailable.

A volunteer took 10 tablets of ERr 731® (dosage=40 mg of ERr 731®) with liquid in the morning (8.00 h). Subsequently, 10 ml of blood was taken at various times (as indicated in FIG. 1) and the plasma was obtained by centrifugation.

These plasma samples were processed as follows: 500 µl of plasma were mixed with 25 µl of an internal standard working solution (2.5 ng/µl rhaponticin or rhapontigenin in methanol) and then mixed with 500 µl of isotonic NaCl solution and 2.5 ml of diethyl ether/butanol (9/1; v/v). After shaking and centrifugation (10 minutes at 4600 rpm), about 2 ml of the supernatant were removed and dried under a stream of nitrogen (at 60° C.). The pellet was taken up in 50 µl of methanol. Addition of 200 µl of distilled water was followed by renewed mixing, and 200 µl were pipetted into autosampler tubes (light-protected). 30 µl of the samples were injected for analysis into an LC-MS/MS system (PE Sciex API 3000). Chromatographic separation of the analytes took place on a Phenomenex Polymer X column with a gradient of an ammonium buffer solution and an acetonitrile/methanol mixture as mobile phase.

Figure 4:
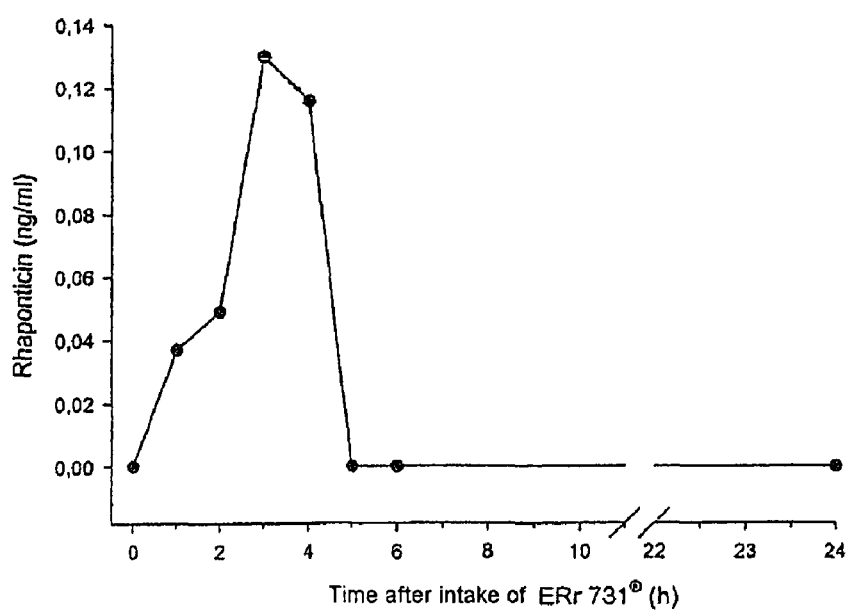
FIG. 4 shows the result of a pharmacokinetic investigation on the ingredient rhaponticin in ERr 731® in the blood of a female subject after oral administration of ERr 731®. Rhaponticin was detectable in the blood, but not rhapontigenin. Likewise, the metabolite thereof piceatannol was undetectable in the blood under the experimental conditions.

The analyzed results are summarized in FIG. 4. Rhaponticin was detected in the blood, with a maximum at 3-4 hours (FIG. 4), whereas rhapontigenin could not be found. Since rhaponticin is one of the main ingredients of ERr 731®, it can be assumed that rhaponticin is an activity-codetermining ingredient of ERr 731®. This is all the more surprising since it was previously assumed that only the aglycones, but not the glycosylated hydroxystilbenes, are active (Park et al., Arch Pharm Res. 2002; 25:528-533).

Test Example 4

Estrogen Receptor β (ERβ) Activation by ERr 731® and its Metabolites in the ERβ-Expressing Endometrial Adenocarcinoma Cell Line HEC-1B HEC-1B cells, a human endometrial adenocarcinoma cell line, do not express either ERα or ERβ. They therefore represent a possible way of investigating, in a human and endometrial context, ligand-dependent effects of substances on the transactivation mechanisms in relation to different receptor subtypes and different estrogen-responsive promoters.

An established ERβ/mC3-luciferase system was employed. For this purpose, HEC-1B cells were applied in 24-well plates with a density of 95 000 cells/well (in Dulbecco's modified Essential Medium (DMEM/F12)). The next day, they were cotransfected with an ERβ-containing construct (hERβ/pSG2) and a triple-ERE-containing promoter/luciferase construct (mC3-Luc/pGL2) (Hillisch et al. Dissecting physiological roles of estrogen receptor alpha and beta with potent selective ligands from structure-based design. Mol Endocrinol. 2004 July; 18:1599-609). The transient transfection took place using DOTAP (N-[1-(2,3-dioleoyloxy)]-N,N,N-trimethylammoniumpropane methyl-sulfate, Roth) as described by the manufacturer.

After 24 hours, the cells were treated with appropriate concentrations of the substances or substance mixtures to be investigated. 17β-Estradiol (E2; 10 nm) served as positive control, and a comparable volume of dimethyl sulfoxide (DMSO) was employed as solvent control. The incubation time was 24 hours. The cells were then lysed. The Luciferase Assay® kit (Promega) was used to determine the luciferase activity on the one hand, and the BCA® kit (Sigma) was used to determine the protein content on the other hand. The resulting specific luciferase activities of the substances to be investigated were then compared with the DMSO control (100%).

At least three transfection experiments were carried out for each test substance. After calculation of the relative luciferase activity in relation to the negative control (DMSO) for each single experiment (set at 100%), the corresponding averages and standard deviations are formed. The results are represented graphically in the form of a bar diagram. Student's test was used to calculate the significance, the latter being fixed as follows: * $p<0.05$;  $p<0.01$; * $p<0.001$.

Figure 5A:
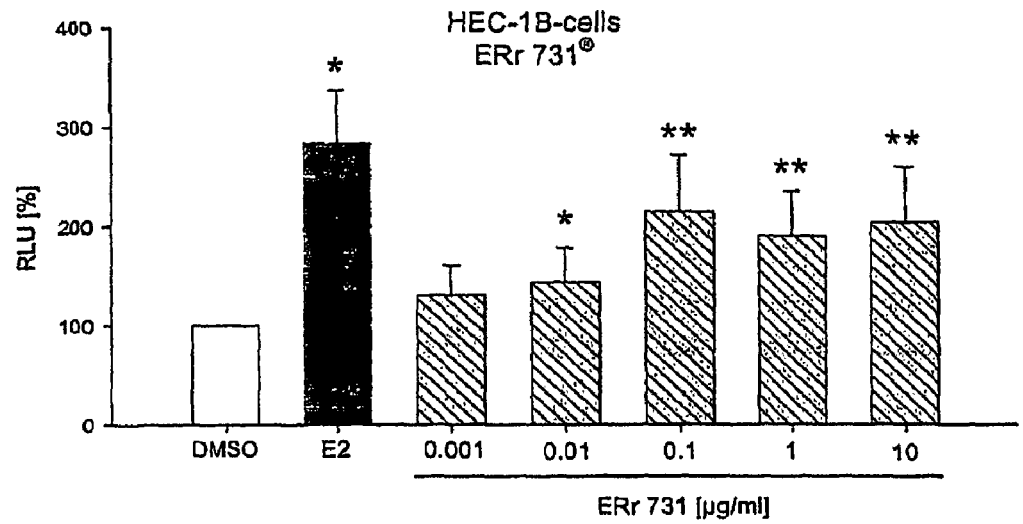
FIG. 5 shows the result of experiments on the activation of the estrogen receptor β (ERβ) by the active ingredient combination ERr 731® in the human endometrial carcinoma cell line HEC-1B (FIG. 5*a*); the aglycones trans-rhapontigenin (FIG. 5*b*) and deoxyrhapontigenin (FIG. 5*c*) are effective only at higher concentrations (E2=estradiol; RLU=relative luciferase units); *=p<0.05;**=p<0.01
Figure 5B:
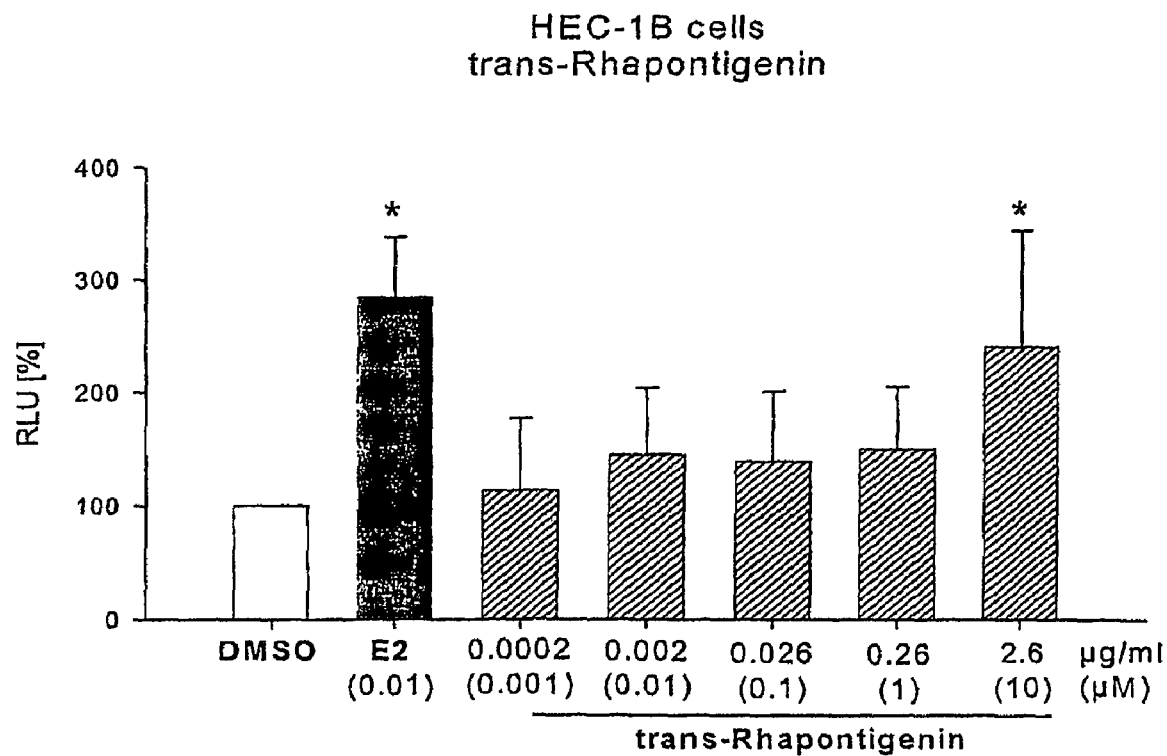
Figure 5C:
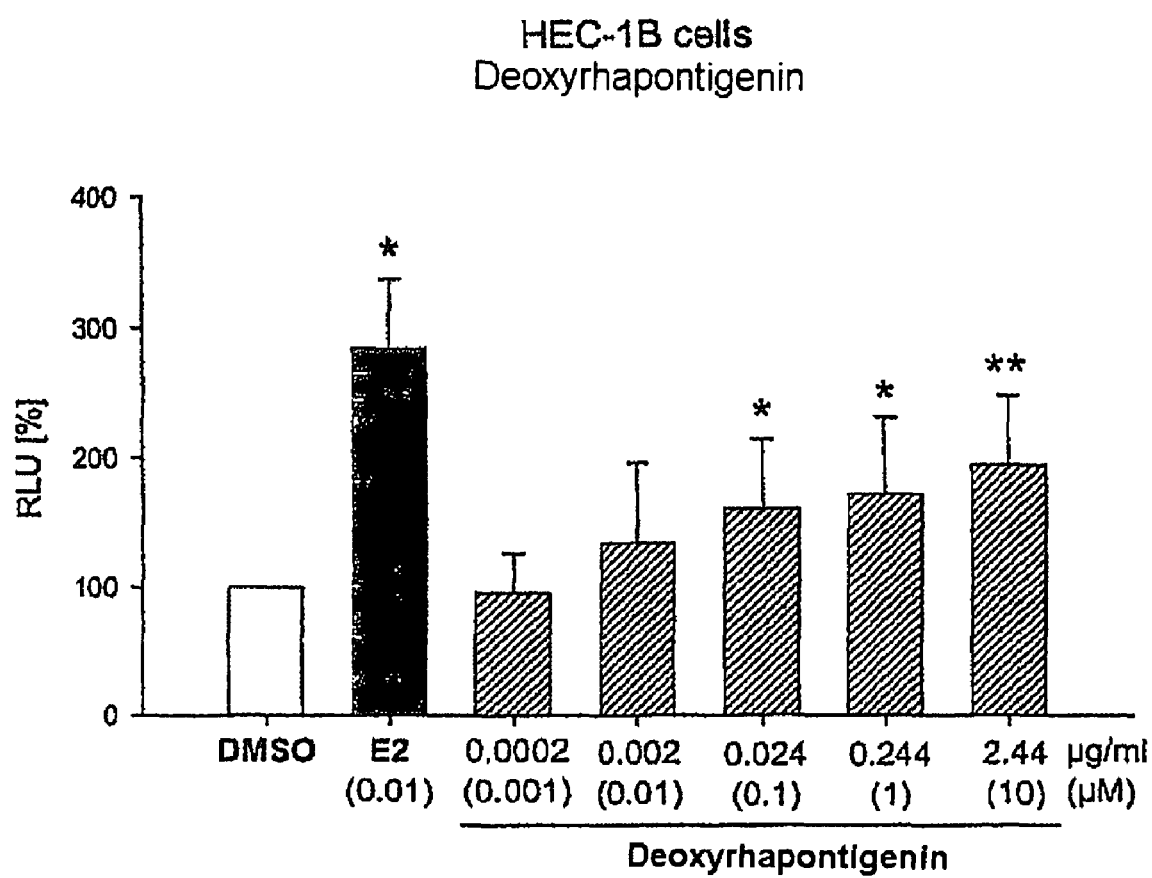

The results for ERr 731® are depicted in FIG. 5a, for trans-rhapontigenin in FIG. 5b and for deoxyrhapontigenin in FIG. 5c. They show that the substances activate the ERβ dose-dependently and thus can be employed according to the invention.

The results of the tests described above demonstrate the surprising finding that, contrary to previous assumptions, the "precursors" of resveratrol and piceatannol, i.e. the glycosides rhaponticin and deoxyrhaponticin (as main constituents of ERr 731®) can be taken up per se by human cells. Skilled workers have previously assumed that these glycones are non-absorbable (cf. Park et al, Arch. Pharm. Res. 2002, 25 (4), 528-533). A further surprising fact is that the active ingredient combination ERr 731® has greater activity than the corresponding aglycones rhapontigenin and deoxyrhapontigenin. In addition the latter are not detectable under physiological conditions (tests not shown).

It has thus been possible to show for the first time by the present invention the direct pharmacological activity of the glycosides rhaponticin and deoxyrhaponticin (as main constituents of ERr 731®).

The invention claimed is:

1. A solid dosage form comprising an active-ingredient-containing solid core with a pharmaceutically acceptable carrier and an active ingredient content of about 1 to 20% by weight, based on the total weight of the core, wherein the active ingredient is a hydroxystilbene-containing active ingredient combination consisting essentially of rhaponticin and deoxyrhaponticin, in a ratio by weight of from 10:1 to 1:10, wherein rhaponticin and deoxyrhaponticin, each independently, are in a form selected from a salt, a phenol form, an ester derivative, and an ether derivative,
wherein said solid dosage form has a total weight in the range of about 150 mg ±20 mg, a core weight of 84 mg ±10 mg, and an active ingredient content of about 3 to 10 mg per dose unit; wherein said solid dosage for has a uniformity of active ingredient content (averaged over 10 randomly selected individual dose units) not exceeding ±5% by weight based on the total weight of the dose unit;
and said solid dosage form is obtained by a method comprising the steps of:
a) adding to the total amount of the active ingredient combination the pharmaceutically acceptable carrier in portions and mixing after each addition of the carrier with a ball mill over a period of from 30 minutes to 3 h; and
b) consolidating the mixture to give the active ingredient core.

2. The solid dosage form as claimed in claim 1, wherein the active ingredient or the active ingredient combination is obtained from roots of *Rheum rhaponticum*.

3. The solid dosage form as claimed in claim 1, where the active ingredient combination consists essentially of rhaponticin and deoxyrhaponticin in a ratio of about 2:28 to 28:2 by weight.

4. The solid dosage form as claimed in claim 1, wherein the active ingredient combination consists essentially of approximately 60-66% by weight rhapontigenin, 30-35% by weight deoxyrhaponticin, 0-2% by weight rhapontigenin; and 0-2% by weight deoxyrhapontigenin.

5. The solid dosage form as claimed in claim 1, wherein the total active ingredient content is about 2 to 20 mg per dose unit.

6. The solid dosage form as claimed in claim 1, wherein the core is lactose-free core.

7. The solid dosage form as claimed in claim 1 in the form of a pill, of a tablet, of an extrudate or of granules.

8. The solid dosage form as claimed in claim 1, which has a gastro-resistant coating.

9. The solid dosage form as claimed in claim 8, wherein the coating comprises substantially no plasticizer.

10. A process for producing a solid dosage unit as claimed in claim 1, comprising:
a) adding to the total amount of the active ingredient combination the pharmaceutically acceptable carrier in portions and mixing after each addition of the carrier with a ball mill over a period of from 30 minutes to 3 h; and
b) consolidating the mixture to give the active ingredient core.

11. The process as claimed in claim 10, wherein the active ingredient or active ingredient combination is dissolved or dispersed in an inert liquid and mixed with the carrier, and the solvent is removed during or after the consolidating step.

12. The process as claimed in claims 10, wherein the active ingredient or the active ingredient combination is prepared by:

a) providing an active ingredient-containing part of a medicinal plant;
b) adding an aqueous extractant thereto;
c) after the extractant has acted, obtaining a liquid extract phase from the mixture; and
d) removing the extractant from the liquid extract phases, thereby preparing the active ingredient combination.

13. The process as claimed in claim 12, wherein the active ingredient-containing part of a medicinal plant is provided in comminuted form.

14. The process as claimed in claim 12, further comprising repeating the extraction several times.

15. The process as claimed in claim 12, wherein the extraction with the aqueous extractant is carried out at a pH of the mixture in the alkaline range.

16. The process as claimed in claim 12, wherein the medicinal plant is selected from plants of the genus *Rheum* sp., *Astragalus* sp., *Cassia* sp. and *Picea* sp.

17. The process as claimed in claim 10, wherein the active ingredient core is provided with a gastro-resistant coating.

18. The process as claimed in claim 17, where the coating comprises substantially no plasticizer.

19. The process as claimed in claim 10, wherein the core is sugar-coated.

20. A pharmaceutical composition comprising a solid dosage form as claimed in 1 and a pharmaceutically acceptable carrier.

21. A method of treating menopausal symptoms, juvenile oligomenorrhea and dysmenorrhea, primary and secondary amenorrhea or endometritis in a subject comprising administering to the subject a solid dosage form, a liquid dosage form or a semisolid dosage form, wherein the solid dosage form, liquid dosage form or semisolid dosage form comprises the hydroxystilbene-containing active ingredient or a hydroxystilbene-containing active ingredient combination as claimed in claim 1.

22. The method of claim 21, wherein the active ingredient or active ingredient combination brings about treatment by selective activation of ERβ.

23. The method of claim 21, wherein the menopausal symptoms occur in peri- or postmenopause.

24. The method of claim 23, wherein the menopausal symptoms are selected from the group consisting of hot flushes, sweating episodes, sleep disorders, irritability, psychological and mental exhaustion, sexual problems and urinary tract symptoms.

25. The method of claim 21, wherein the menopausal symptoms are the result of natural or therapeutically induced menopause.

26. A method for selective activation of ERβ in vivo or in vitro comprising contacting a cell with the solid dosage form comprising a hydroxystilbene-containing active ingredient combination as claimed in claim 1.

27. The solid dosage form of claim 1, wherein said pharmaceutically acceptable carrier is a cellulose-based carrier.

28. The solid dosage form of claim 27, wherein said cellulose-based carrier is microcrystalline cellulose.

* * * * *